(12) United States Patent
Siffert et al.

(10) Patent No.: US 9,255,297 B2
(45) Date of Patent: Feb. 9, 2016

(54) CHK2 POLYMORPHISM AS A CANCER MARKER

(75) Inventors: Winfried Siffert, Gelsenkirchen (DE); Kathrin Riemann, Essen (DE)

(73) Assignee: Universitaet Duisburg-Essen, Essen (DE)

( * ) Notice: Subject to any disclaimer, the term of this patent is extended or adjusted under 35 U.S.C. 154(b) by 520 days.

(21) Appl. No.: 13/254,725

(22) PCT Filed: Mar. 8, 2010

(86) PCT No.: PCT/EP2010/052894
§ 371 (c)(1), (2), (4) Date: Mar. 19, 2012

(87) PCT Pub. No.: WO2010/100279
PCT Pub. Date: Sep. 10, 2010

(65) Prior Publication Data
US 2012/0171671 A1 Jul. 5, 2012

(30) Foreign Application Priority Data
Mar. 6, 2009 (EP) ..................... 09154527

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/112* (2013.01); *C12Q 2600/118* (2013.01); *C12Q 2600/136* (2013.01); *C12Q 2600/172* (2013.01)

(58) Field of Classification Search
None
See application file for complete search history.

(56) References Cited

U.S. PATENT DOCUMENTS

2010/0129797 A1* 5/2010 Riemann et al. ............... 435/6

OTHER PUBLICATIONS

Weiker et al. (Naunyn-Schmiedebergs Archives of Pharmacology, (Apr. 2009) vol. 379, Supp. [1], pp. 44-44.).*
Einarsdottir et al. (PLoS Med 3(6): e168. DOI: 10.1371/journal.pmed.0030168) pp. 895-903 and table S8.*
Hegele Arterioscler Thromb Vasc Biol 2002;22;1058-1061.*
Evans (Science 1999 vol. 286 pp. 487-491.).*
Antoni et al. Nature Reviews, vol. 7, Dec. 2007, pp. 925-936.*
Baynes et al. Breast Cancer ResearchDec. 2007, vol. 9, R27, pp. 1-14.*
Zill et al. Molecular Psychiatry (2004) 9, 1030-1036.*
Nguyen-Dumont et al. BMC Medical Genomics 2011, 4:39, 10 pages.*
Gu et al. Mol Biol Rep (2012) 39:5977-5984.*
Zhang et al. Carcinogenesis vol. 31 No. 7 pp. 1251-1258, 2010.*
Cybulski et al. Am. J. Hum. Genet. 75:1131-1135, 2004.*
dbSNP record for rs2236141. obtained from http://www.ncbi.nlm.gov on Jul. 18, 2014, eight pages.*
dbSNP record for rs2236142. obtained from http://www.ncbi.nlm.gov on Jul. 18, 2014, three pages.*
Simon et al. (Neurosurgery 59:1078-1085, 2006).*
Dai et al. (BMC Medical Genomics 2008, 1:24, eighteen pages).*
GenBank Record having accession AY800241, Nov. 6, 2004 (Homo sapiens CHK2 checkpoing homolog (S. pombe)(CHEK2) gene, complete cds. NIEHS-SNPs, Environmental Genome project, NIEHS ES15478, Department of Genomic Sciences, Seattle, WA).*
Antoni Laurent et al"CHK2 kinase: cancer susceptibility and cancer therapy—two sides of the same coin?" Nature Reviews Cancer, vol. 7, No. 12, Dec. 2007, pp. 925-936.
Zhang Peilin et al: "Methylation of CHK2 gene promoter silences transcription in non-small cell lung cancer leading to natural resistance to cisplatin," Proceedings of the American Association for Cancer Research Annual Meeting, vol. 45, Mar. 2004, p. 70.
Einarsdottir Kristiana et al: "Linkage disequilibrium mapping of CHEK2: common variation and breast cancer risk," PLOS Medicine Jun. 2006, vol. 3, No. 6, Jun. 2006, p. E168.
Kato N et al: "Regulation of Chk2 gene expression in lymphoid malignancies: involvement of epigenetic mechanisms in Hodgkin's lymphome cell lines", Cell Death and Differentiation, vol. 11, No. Suppl. 2, Dec. 2004, pp. S153-S161.
Baynes Caroline et al: "Common variants in the ATM, BRCA1, BRCA2, CHEK2 and TP53 cancer susceptibility genes are unlikely to increase breast cancer risk", Breast Cancer Research, Current Science, London, GB, vol. 9, No. 2, Apr. 11, 2007, p. R27.

* cited by examiner

*Primary Examiner* — Juliet Switzer
(74) *Attorney, Agent, or Firm* — Fanelli Haag PLLC

(57) ABSTRACT

The invention relates to the use of gene modifications in the human gene CHK2 (CHEK2), which encodes the checkpoint kinase 2, for predicting the risk and progression of cancer diseases, for predicting the response to pharmacological or non-pharmacological therapeutic measures for treating cancer diseases, and for predicting undesired effects of drugs. The invention further relates to the provision of individual gene variants with the help of which further gene modifications that can be used for the aforementioned purposes can be detected and validated. Such gene modifications can comprise a substitution of adenine for guanine in position −7161 in the promoter of CHK2, a substitution of guanine for cytosine in position −7235, a substitution of adenine for guanine in position −10532, or a deletion of 29 base pairs in positions −10621 to −10649.

5 Claims, 11 Drawing Sheets

SEQUENCE LISTING

```
<160> NUMBER OF SEQ ID NOS: 17

<210> SEQ ID NO 1
<211> LENGTH: 10
<212> TYPE: DNA
<213> ORGANISM: Homo sapiens

<400> SEQUENCE: 1
ggtccggcgg                                                          10

<210> SEQ ID NO 2
<211> LENGTH: 20
<212> TYPE: DNA
<213> ORGANISM: Homo sapiens

<400> SEQUENCE: 2
cctcattggt ccggcggcag                                               20

<210> SEQ ID NO 3
<211> LENGTH: 20
<212> TYPE: DNA
<213> ORGANISM: Homo sapiens

<400> SEQUENCE: 3
cctcattggt ccagcggcag                                               20

<210> SEQ ID NO 4
<211> LENGTH: 15
<212> TYPE: DNA
<213> ORGANISM: Homo sapiens
```

```
<400> SEQUENCE: 4
ctctcccttc taaac                                                    15

<210> SEQ ID NO 5
<211> LENGTH: 10
<212> TYPE: DNA
<213> ORGANISM: Homo sapiens

<400> SEQUENCE: 5
ctctcccttc                                                          10

<210> SEQ ID NO 6
<211> LENGTH: 12
<212> TYPE: DNA
<213> ORGANISM: Homo sapiens

<400> SEQUENCE: 6
gctctccctt ct                                                       12

<210> SEQ ID NO 7
<211> LENGTH: 20
<212> TYPE: DNA
<213> ORGANISM: Homo sapiens

<400> SEQUENCE: 7
tccgctctcc cttctaaact                                               20

<210> SEQ ID NO 8
<211> LENGTH: 20
<212> TYPE: DNA
<213> ORGANISM: Homo sapiens

<400> SEQUENCE: 8
tccgctctgc cttctaaact                                               20

<210> SEQ ID NO 9
<211> LENGTH: 10
<212> TYPE: DNA
<213> ORGANISM: Homo sapiens

<400> SEQUENCE: 9
actctggaga                                                          10

<210> SEQ ID NO 10
<211> LENGTH: 10
<212> TYPE: DNA
<213> ORGANISM: Homo sapiens

<400> SEQUENCE: 10
ctctagagag                                                          10

<210> SEQ ID NO 11
<211> LENGTH: 20
<212> TYPE: DNA
<213> ORGANISM: Homo sapiens

<400> SEQUENCE: 11
taagatactc tggagaggaa                                               20

<210> SEQ ID NO 12
<211> LENGTH: 20
<212> TYPE: DNA
```

```
<213> ORGANISM: Homo sapiens

<400> SEQUENCE: 12
taagatactc tagagaggaa                                              20

<210> SEQ ID NO 13
<211> LENGTH: 11
<212> TYPE: DNA
<213> ORGANISM: Homo sapiens

<400> SEQUENCE: 13
catcttgacc a                                                       11

<210> SEQ ID NO 14
<211> LENGTH: 10
<212> TYPE: DNA
<213> ORGANISM: Homo sapiens

<400> SEQUENCE: 14
ggtcttgaac                                                         10

<210> SEQ ID NO 15
<211> LENGTH: 50
<212> TYPE: DNA
<213> ORGANISM: Homo sapiens

<400> SEQUENCE: 15
gtagaggcgg ggtttcacca tcttgaccag gctggtcttg aactcctgac              50

<210> SEQ ID NO 16
<211> LENGTH: 10
<212> TYPE: DNA
<213> ORGANISM: Homo sapiens

<400> SEQUENCE: 16
ggggtttcct                                                         10

<210> SEQ ID NO 17
<211> LENGTH: 21
<212> TYPE: DNA
<213> ORGANISM: Homo sapiens

<400> SEQUENCE: 17
gtagaggcgg ggtttcctga c                                            21
```

CHK2 POLYMORPHISM AS A CANCER MARKER

CROSS REFERENCE TO RELATED APPLICATIONS

Figure 1:
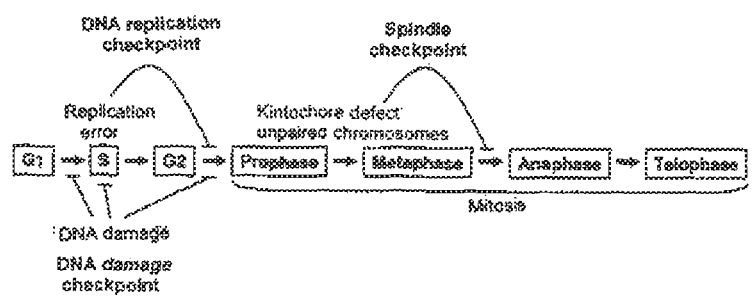

This application is a National Stage of PCT/EP2010/052894, filed Mar. 8, 2010 which claims priority to European Patent No. 09154527.7, filed Mar. 6, 2009, the disclosures of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 19, 2012, is named 54UD1US1.txt and is 2,755 bytes in size.

The invention relates to a diagnostic method for the determination of a suitable therapy for treating a cancer disease.

An essential aspect of cancer therapy is in the first place the establishment of an exact diagnosis. The diagnosis provides knowledge as to the actual stage of the disease, which is also decisive with respect to the kind of therapy that is to be used subsequently, e.g. surgical removal of the tumour and optionally radiation and pharmacological therapy, possibly also using physical methods (e.g. hyperthermia). The classic method for diagnosis includes the so-called "staging" and "grading". Staging describes the size of the tumour and its invasiveness and examines whether lymph nodes are affected and whether there are distant metastases (e.g. TNM staging system). Grading is the histological examination of the tumour cells wherein lower malignant potential is attributed to highly differentiated tumour cells than to poorly differentiated or dedifferentiated cells. This classification is limited with respect to the prediction for the individual patient and clinical experience has shown that patients with the same tumour stage show clearly different courses of disease and different responses to a therapy, which is ultimately clear from the extremely varying survival periods.

For this reason, clinical practice requires the provision of additional and more precise markers which allow improved individual prognosis for a cancer disease. This can be realised by using histochemical markers as in the analysis of oestrogen receptor expression in the case of breast cancer.

An alternative approach is the search for gene defects, e.g. somatic mutations in tumour suppressor genes. New approaches try to predict the course of the disease by means of gene expression profiles. Another problem in cancer treatment is the prediction regarding the effectiveness of cancer drugs, the individual optimum dosage or duration of therapy but also the prediction of the occurrence of serious and dangerous side effects. For example, the fact that some patients undergoing a therapy treatment with irinotecan suffer from severe adverse effects can be attributed to genetic polymorphisms in the UGT1A1 gene. Prior gene analysis allows to identify such patients before the beginning of therapy and to adjust the dosage.

Moreover, therapies using medicaments that are produced with biotechnological methods are expensive and, in future, will be limited to patients where efficacy of the treatment seems to be probable due to their individual disposition.

Basic Properties of Malignant Tumours

Cancer cells are characterised by the loss of contact inhibition and uncontrolled cell growth. Such modifications are caused spontaneously or by noxae, so-called carcinogens which damage the genome. Such noxious substances include many chemical substances, tobacco smoke but also UV light. Furthermore, genetic factors play a prominent role in the development of cancer. Apart from the unrestrained growth, the tendency to form "daughter tumours" (metastases) in other organs is characteristic of cancer cells. The metastases are regularly spread via the blood or lymph vessels. In a majority of cases, cancer diseases are incurable and lethal. Therapeutical measures aim at the surgical removal of the primary tumour and the metastases. Furthermore, it is possible to treat tumours with radiation. So-called cytostatic agents, antibodies against specific proteins or surface marker or immune-modulating substances (cytokines, interferons), are used to try to kill the rapidly proliferating cells or to induce apoptosis.

It is of great relevance to define prognosis factors for the course of cancer diseases which provide information on the response to specific forms of therapy or which allow general prediction regarding the occurrence of metastases, tumour progression and survival.

Obviously, there is a plurality of individual, undiscovered biological variables which determine the course of a tumour disease independently of staging and grading. These factors include genetic host factors. It is further desirable to develop genetic markers which allow prediction regarding the occurrence of tumours. Markers of this kind serve the purpose of including persons concerned in further screening measures (serology, radiography, ultrasonography, MRT etc.) in time. This allows to diagnose and treat cancer diseases at an early stage with the chances of recovery and survival being significantly higher for tumours at an early stage than for tumours at an advanced stage.

The Significance of DNA Repair Mechanisms

Due to DNA repair mechanisms, cells are able to eliminate defective modifications of the DNA structure. Such damages in the DNA can be caused spontaneously during DNA replication or through the influence of mutagenic substances, extreme heat or ionizing radiation. DNA damages can result in DNA replication for mitosis taking place in a wrong way, in proteins being no longer synthesized or in a wrong way or in essential chromosomal regions being cleaved after double-strand breaks. If the complex repair mechanisms of the cell are not successful, the number of defects accumulating in proliferating and dormant somatic cells increases so much that normal cell functions are defective. In a germinal cell, the daughter cells would no longer be viable, which leads to an inactivation of the cell line: the cell or the second to the third successive generation, respectively, loses the capability of cell division and dies. Within cell cycle control, control proteins are able to recognise a cell or its DNA as being defect and to induce cell cycle arrest or programmed cell death (apoptosis).

The Significance of Checkpoint Kinase 2

The most important function of a cell is to maintain genomic integrity. For this reason there are various control mechanisms that ensure that all processes within the cell cycle are terminated correctly. These control mechanisms are referred to as "checkpoints". These are not well defined points, as the term implies, by but a reaction cascade that can be initiated under specific conditions.

Several cell cycle checkpoints have been characterised so far. The best-investigated checkpoints in mammals are illustrated in FIG. 1. On the one hand, there is the DNA damage checkpoint which can be activated by damage to the DNA in different phases of the cell cycle. This damage can be induced by exogenous causes, such as radiation, as well as by endogenous events, e.g. spontaneous mutations. On the other hand, the replication checkpoint is activated by incomplete or defective DNA replication. The spindle checkpoint controls the formation of the bipolar spindle, the attachment of kinetochores and the formation of centromere structures.

As long as these processes are not completely terminated or the damage is not repaired, the transition of the cell into the next phase of the cell cycle is inhibited in order to ensure that the genomic integrity of the cell is maintained.

Figure 2:
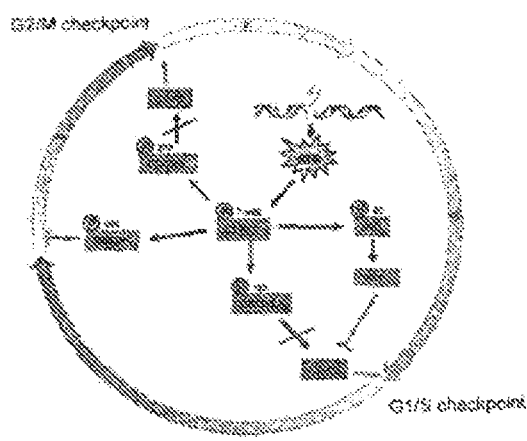

Checkpoint kinase 2 is involved in essential control mechanisms in the cell cycle, which ensure that the transmission of errors to daughter cells is minimised. The relevant CHK2 reaction cascades that are activated at different checkpoints are illustrated in FIG. 2. Due to DNA damage, ATM (ataxia-telangiectasia, mutated) is phosphorylated and, thus, activated. ATM in turn activates CHK2 via phosphorylation at a threonine (Thr) at amino acid position 68. This phosphorylation is a precondition for the capability of dimer formation through which CHK2 can autophosphorylate. It is only in this way that CHK2 can be present in fully activated form and activate its effectors by which a cell cycle arrest during the G1-, S- or G2/M-phase, activation of the DNA repair system or apoptosis can be induced in defect cells.

The effectors of CHK2 include p53 (tumor protein 53) which is phosphorylated by CHK2 at serine (Ser) 20 and becomes stable thereby. Subsequently, p53 positively regulates factors involved in the repair of DNA damages, apoptosis and the control of the cell cycle. BRCA1 (breast cancer 1 gene) also belongs to the CHK2 substrates. It is phosphorylated by CHK2 at Ser988 and, thus, it is released from the complex with CHK2, which in turn results in stopping the cell cycle in order to repair damaged DNA. CDC25C (cell division cycle 25C) is also phosphorylated by CHK2 at Ser216, whereby its own phosphatase activity is inhibited and it is degraded in a cytoplasmic manner. In this case, Cdk1 (cyclin-dependent kinase 1) cannot be activated and, thus, it is avoided that cells with damaged DNA enter into mitosis. Moreover, CDC25A is phosphorylated by CHK2 at Ser123 upon which it ubiquitinates and is degraded in proteasome-dependent manner. This protein plays an important role with regard to the progression of the cell in the cell cycle, however, inhibited by the degradation.

CHK2 plays an important role in signal transduction initiated by DNA damage. The physiological significance of CHK2 was analysed by generating knock out mice. Chk2$^{-/+}$ as well as Chk2$^{-/-}$ mice were viable. However, after a radiation with sublethal doses (8 Gy), they showed survival periods of different length: the median survival period of wildtype and Chk2$^{-/-}$ mice was significantly shorter than that of Chk2$^{-/-}$ mice. Thus, Chk2$^{-/-}$ mice showed radio resistance which was caused by a reduced radiation-induced apoptosis rate. Whereas the G2/M checkpoint was not affected in Chk2$^{-/-}$ mice, the G1/S checkpoint could not be maintained although it was possible to induce it. This is caused to a reduced transcriptional activity of p53. Moreover, tumours developed only in Chk2$^{-/-}$ mice, in contrast to mice having at least one functional Chk2 allel.

Thus, the problem underlying the present invention is to provide a method allowing improved prognosis of the natural history of a cancer disease and the response to any form of therapy. In particular, this method should also allow to identify patients whose increased DNA repair mechanisms make cancer therapy difficult.

This problem is solved by an in vitro method for the prediction of the risk to develop a cancer disease, the course of the disease, the effectiveness of the drug and the drug-related risk in the treatment of a cancer disease wherein one or more gene modification(s) are searched for in the promoter region of the CHK2 gene on the human chromosome 22q12.1 in a sample of a patient and the gene modification is selected from the polymorphism −7161G>A, the polymorphism −7235C>G, the polymorphism −10532G>A and the polymorphism −10649-(−10621)del29.

The use of the above-mentioned polymorphisms for the aforementioned purposes is also subject matter of the invention.

Thus, the invention aims at a. providing function-modifying genomic polymorphisms in the promoter of the gene CHK2 which either lead to a modification of protein expression or to a modification of the expression of splicing variants or b. which are suited to find and/or validate further polymorphisms or haplotypes, respectively, in the gene CHK2, c. providing polymorphisms which are suited to predict in general risks and courses of diseases, d. providing polymorphisms which are suited to predict in general responses to pharmaceuticals and cancer therapies, in particular CHK2 inhibitors, and side effects, e. providing polymorphisms which are suited to predict in general the effect of other forms of therapy (such as radiation, heat, cold).

Due to the fundamental significance of CHK2 for the maintenance of the genomic integrity, polymorphisms of this kind are suited to predict in general risks of disease and/or courses of disease in the case of cancer diseases and/or to predict responses to therapy/failure of therapy or undesired side effects for all pharmaceuticals or non-pharmacological therapies.

Detection of Polymorphisms in the Promoter of the Gene CHK2

Three polymorphisms in the promoter region of the gene CHK2 are known and they can be found in databases that are generally accessible. It was by systematic sequencing of DNA samples of humans that these three polymorphisms were detected and validated: −7161G>A (rs2236141), −7235C>G (rs2236142) and −10532G>A (rs5762767) (FIG. 5). For this purpose, gene sequences of the promoter region of CHK2 were amplified by PCR reaction and sequenced using the method according to Sanger. The methods necessary for this purpose, e.g. deriving the primer pairs that are required for the PCR reaction and selecting the sequencing primers are well known to the person skilled in the art. In this context, a new polymorphisms was found which is a deletion of 29 base pairs (−10649-(−10621)del29, no dbSNP ID) (FIG. 5). The numbering of these SNPs is such that number +1 is assigned to the nucleotide A of start codon ATG. Since it is understood that number 0 does not exist, number −1 is assigned to the nucleotide preceding the A of start codon ATG.

The detection of this polymorphisms according their use according to the invention can be carried out by means of any methods known to the person skilled in the art, e.g. direct sequencing, PCR with subsequent restriction analysis, reverse hybridisation, dot-blot or slot-blot method, mass spectrometry, Taqman® or LightCycler® technology, Pyrosequencing®, Invader® technology, Luminex method. Moreover, these gene polymorphisms can be detected at the same time by means of multiplex hybridisation and hybridisation to a DNA chip.

In principle, all cells of the human body can generate in a malignant manner and result in a cancer disease. The explanations, here and below, describe general mechanisms of tumour progression, metastatization and response to therapy. In this respect, the mechanisms described herein and the claims relate to all human tumours. The following are only listed as examples.

Tumours of the urogenital tract such as renal cell carcinoma, prostate carcinoma and seminoma; tumours of the female reproductive system such as breast cancer, uterine corpus carcinoma, ovarian carcinoma, cervical carcinoma; tumours of the gastrointestinal tract such as carcinoma of the oral cavity, oesophageal carcinoma, gastric carcinoma, liver carcinoma, bile duct carcinoma, pancreatic carcinoma, colon carcinoma, rectal carcinoma; tumours of the respiratoral tract such as laryngeal carcinoma, bronchial carcinoma; tumours of the skin such as malignant melanoma, basalioma, and t-cell lymphoma; tumour diseases of the hematopoietic system such as Hodgkin and non-Hodgkin lymphomas, acute and chronic leukaemias, plasmacytoma; tumour diseases of the brain and the nervous tissue, respectively, such as glioblastoma, neuroblastoma, medulloblastoma, meningeal sarcoma, astrocytoma as well as soft tissue tumours such as sarcoma and head and neck tumours.

The Gene CHK2

Figure 3:
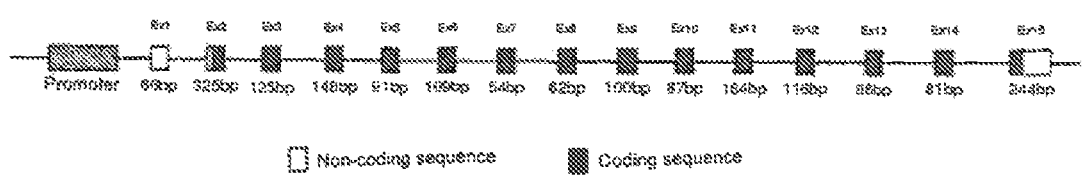

The human gene GHK2 is located on chromosome 22q12.1 (Genebank accession number NM__007194) and encodes an protein of 65 kD size which is expressed in the nucleus. In this context, it is pointed out that the gene is referred to as "CHK2" and as "CHEK2". In the following, the designation "CHK2" is used. A schematic illustration of the gene structure can be found in FIG. 3. The active promoter region of CHK2 has already been characterised. The promoter sequence contains numerous binding sites for the transcription factor SP1 the binding of which reinforces transcriptional activity. A positive regulation of CHK2 was also observed upon NF-Y binding to CCAAT boxes.

Somatic Mutations in CHK2

CHK2 is considered to be a potential tumour suppressor gene since it plays an important role in checkpoint arrest after DNA damage and since different tumour suppressor genes are substrates of CHK2. So far, it was possible to detect somatic mutations in this gene in some patients with sporadic tumours, e.g. colorectal tumours, lung carcinoma, prostate carcinoma, breast cancer as well as in patients with the Li-Fraumeni syndrome, a multi-tumour phenotype. In contrast to single nucleotide polymorphisms (SNPs), these mutations are for example not found in peripheral blood cells of the relevant patients.

Risk of Tumour Diseases Due to Modifications in CHK2

So far, it has been possible in several cases to detect genetic modifications in CHK2 with different tumour diseases and to associate these with the risk of developing the disease. These were not frequent genetic variants but rare mutations (frequency <1%) which could be detected more often in large patient collectives than in healthy control groups. Up to present, only one study has been published which analyses not only these rare mutations but also frequently occurring SNPs. In this context, promoter polymorphism −7161G>A (rs223641) was also analysed with respect to the risk of developing a breast cancer. It was, however, not possible to detect an association (Baynes et al. Common variants in the ATM, BRCA1, BRCA2, CHEK2 and TP53 cancer susceptibility genes are unlikely to increase breast cancer risk. 2007 Breast Cancer Res 9:R27).

CHK2 Inhibitors as Chemotherapeutic Agents

Since checkpoints are involved in many regulatory cascades, they are a suitable target for cancer drugs. Specific properties of the checkpoint proteins account for this: (1) the complex signal transduction system of checkpoints offers a multitude of targets for attack, (2) in healthy cells, some of the checkpoints seem to have only minor significance, which greatly reduces the toxicity of the inhibitors, (3) the restoration of defect checkpoints might result in a slowdown of cell growth, (4) checkpoints as signal transduction system are subject to adaptation which might be interrupted and (5) the restoration of impaired checkpoints might increase the apoptosis rate of cancer cells and, thus, their sensitivity to specific substances.

Contrary to these objectives which will be probably achieved most easily by using a gene therapy approach, two other properties of checkpoints are targets that are more easily to realise. Cells having defect checkpoints show either increased sensitivity or increased resistance to radiation and cytotoxic substances. The inhibition of CHK2 seems to sensitize in particular p53-deficient cells with regard to DNA-damaging agents and, at the same time, it protects the normal tissue from damage and, thus, side effects. For this reason, the inhibition of CHK2 is part of a promising approach to develop new anti-cancer drugs.

Figure 4:
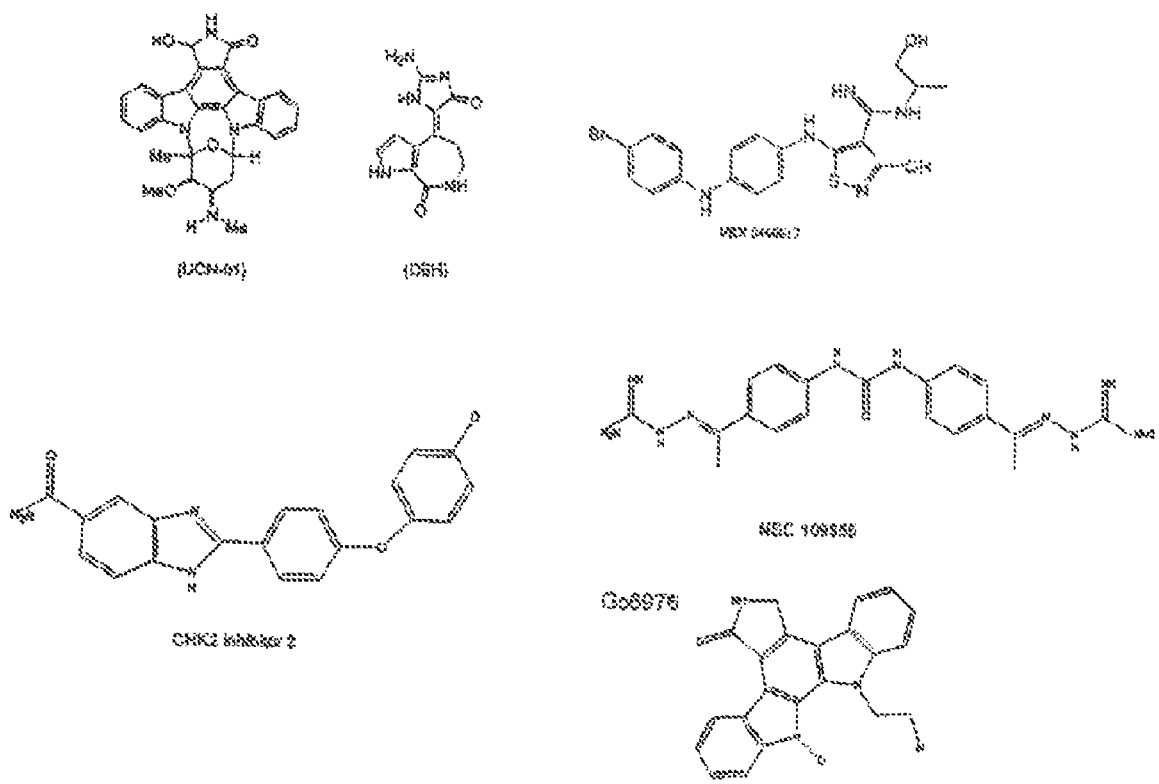

Different CHK2 inhibitors are already known or have already been developed, respectively. At present, apart from the rather unspecific inhibitors UCN-01 and DBH (debromohymenialdisine), specific potent CHK" inhibitors are also available. These include CHK2 inhibitor 2 (2-(4-(4-chlorophenoxy)phenyl)-1H-benzo(d)imidazole-5-carboxamide, VRX0466617 (5-(4-(4-bromophenylamino)phenyl-amino)-3-hydroxy-N-(1-hydroxypropan-2-yl)isothiazole-4-carboximidamide) und NSC 109555 ((2E,2'E)-2,2-(1,1'-(4,4'-carbonyl-bis(azanediyl)bis(4,1-phenylene))bis(ethane-1-yl-1-ylidene))bis(hydrazinecarboximidamide) which are able to contribute to the reduction of side effects during radiotherapy (FIG. 4).

CHK2 Activators as Chemotherapeutical Agents

It is however possible that CHK2 activators may be an alternative in cancer therapy. CHK2 plays a role in the suppression of oncogenesis and its activation can induce tumour cells to leave the proliferative state and to die if no DNA-damaging agents are present. Furthermore, this will induce a strong G2 arrest. The activation strategy might be able to compensate for a disadvantage of the inhibitors: tumours are very heterogenous and for this reason it not always suffices to deactivate only one signal cascade. This heterogeneity could be counteracted by overactivation of maintained cell cycle mechanisms which are common to many types of tumour cell.

Distribution of the −7161G>A, −7235C>GT, −10532G>A and −10649-(−10621)del-29 Polymorphisms, Detection of Haplotypes and Use of these Genotypes in Order to Find Further Relevant Polymorphisms and Haplotypes For this purpose, different DNA samples of Caucasians were genotyped. The result is shown in the following Table:

| polymorphism | genotypes | | |
|---|---|---|---|
| −7161G > A | GG: 188 | GA: 43 | AA: 4 |
| −7235C > G | CC: 25 | CG: 88 | GG: 121 |
| −10532G > A | GG: 188 | GA: 43 | AA: 4 |
| −10649 − (−10621)del29 | II: 56 | ID: 109 | DD: 56 |

I = insertion, D = deletion

Further analyses showed for these DNA samples of healthy Caucasians a linkage disequilibrium between specific polymorphisms. The term linkage disequilibrium refers to the occurrence of allele combinations (haplotypes) which, statistically, occur clearly more frequently or more rarely in combination than this could be expected with respect to their frequency. In this context, it was observed that polymorphisms −7161G>A and −10532G>A link completely to one another. Polymorphisms −7235C>G and −10649-(−10621) del29, in contrast, do not link to each other and only to a limited degree to the other two variants (FIGS. 6A and B). The quality of the linkage is described by the values D' and $r^2$. D'=1 and $r^2$=1 are referred to as significant linkage. The closer these values are to 1, the closer the linkage disequilibrium. The calculation of haplotypes which can be constructed from these four polymorphisms resulted in seven different allele combinations. There is no preferential haplotype resulting from these promoter variants (FIG. 6C). In order to determine all possible combinations, it is necessary to detect at least three of the four polymorphisms.

It is one subject matter of the invention that these new polymorphisms can be used to detect and validate further relevant genomic gen modifications in CHK2 or the neighbouring genes which are, for example, in linkage disequilibrium with genotypes in the gene GHK2. These may also be genes which are also located on chromosome 22, however, at a far distance from the gene CHK2. For this purpose, the following approach is used:

1. For specific phenotypes (such as cellular properties, states of disease, courses of disease, response to pharmaceutical compositions), an association with the polymorphisms −7161G>A, −7235C>G, −10532G>A and −10649-(−10621)del29 is established, wherein these associations can be established individually for each genotype or by using all permutations of the haplotypes.
2. With respect to newly detected gene modifications in CHK2 or neighbouring genes, it is examined whether already existing associations are enhanced or reduced by using the above-described genotypes or haplotypes.

In the following, the Figures will be briefly discussed.

FIG. 1: Schematic representation of the cell cycle with the most important checkpoints FIG. 2: Graphic representation of the reaction cascade at the CHK2-regulated checkpoints FIG. 3: Intron/exon structure of the human gene CHK2 (not true to scale)

FIG. 4: Structural formula of some of the CHK2 inhibitors

FIG. 5: Schematic representation of the polymorphisms in the gene CHK2 (not true to scale)

Figure 6:
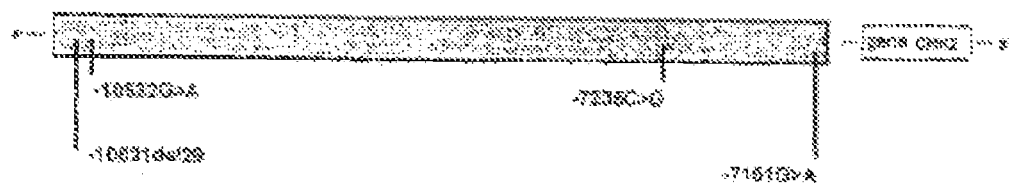

FIG. 6: Linkage analyses of the promoter polymorphisms of CHK2 using the program Haploview; A—graphical representation of the linkage of the polymorphisms to one another. Black squares indicate $r^2$=1; grey squares indicate $r^2$<0.5 and light grey squares indicate $r^2$<0.1. B—frequencies and linkage possibilities of the individual alleles; C—frequencies of the haplotypes constructed; allele designated by a triangle are referred to as so-called haplotype-tagging alleles, i.e. these alleles have to be determined in order to determine the haplotypes.

Figures 6, 7:
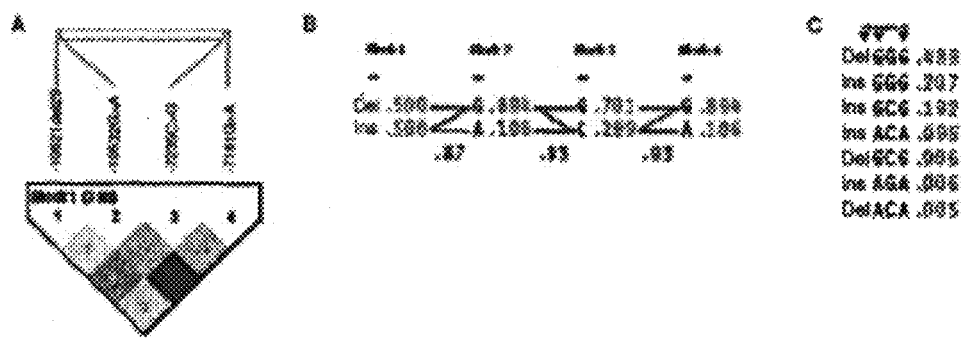

FIG. 7: Putative binding sites for transcription factors in the promoter of the gene CHK2; bases indicated in red represent the alleles of the relevant polymorphism. FIG. 7 discloses SEQ ID NOS 1-17, respectively, in order of appearance.

Figure 8:
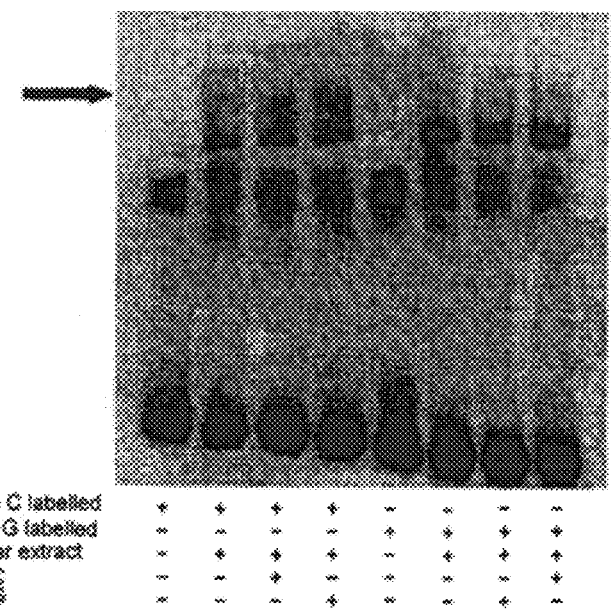

FIG. 8: Result of the Electrophoretic Mobility Shift Assay (EMSA) with constructs containing the different alleles of the −7235C>G polymorphism of CHK2. After addition of cell nuclear extract, increased binding of nuclear protein to the C allele is observed. The binding is specifically inhibited by the presence of a displacing oligonucleotide.

Figure 9:
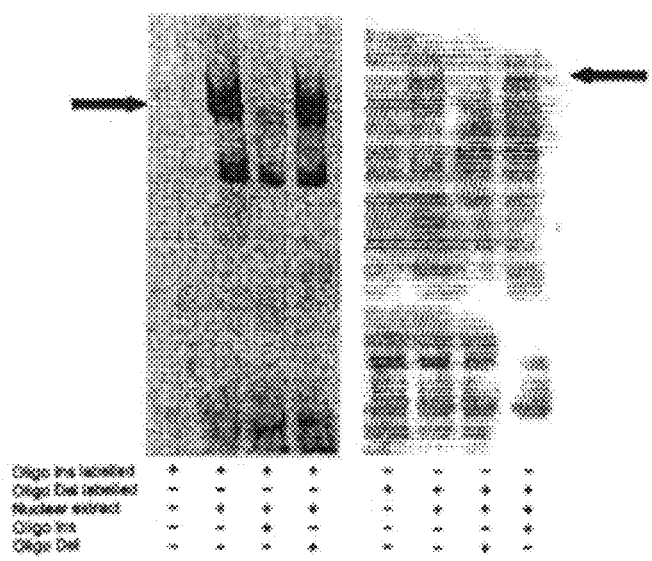

FIG. 9: Result of the Electrophoretic Mobility Shift Assay (EMSA) with constructs containing the different alleles of the −10649-(−10621)del29 polymorphism of CHK2. After addition of cell nuclear extract. It is observed that both alleles result in the binding of a transcription factor, with which the second allele can compete. However, the transcriptions factors differ in this case.

Figure 10:
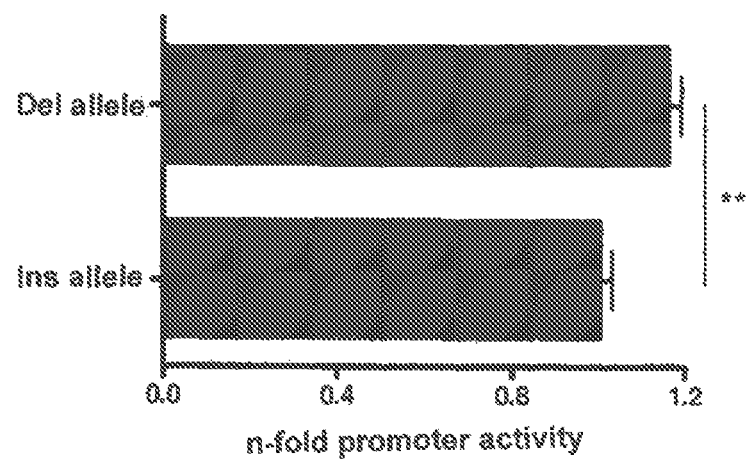

FIG. 10: CHK2 promoter activity in dependence on the −10649-(−10621)del29 polymorphism as determined by SEAP reporter assays; : $p<0.01$ FIG. 11: Expression of CHK2 mRNA depending on the −7161G>A polymorphism. The quotient CHK2-/β-actin-mRNA is shown. A: breast cancer, B: CLL; : $p<0.01$; *: $p<0.05$ FIG. 12: Expression of CHK2 mRNA depending on the −7235C>G polymorphism. The quotient CHK2-/β-actin-mRNA is shown. A: breast cancer, B: CLL; **: $p<0.05$ FIG. 13: Expression of CHK2 mRNA depending on the −10649-(−10621)del29 polymorphism in female patients suffering from breast cancer. The quotient CHK2-/β-actin-mRNA is shown.

Figure 14:
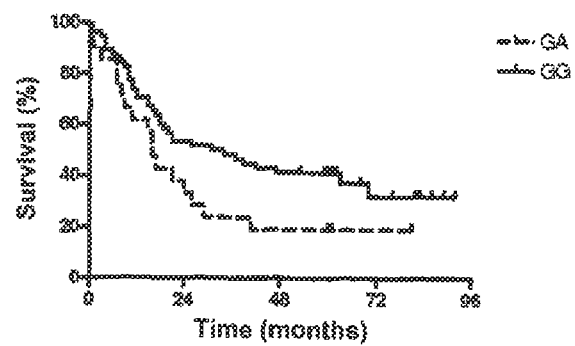

FIG. 14: Kaplan-Meier analysis regarding the survival of patients suffering from colorectal carcinoma depending on the genotype of the −7161G>A polymorphism.

Figure 15:
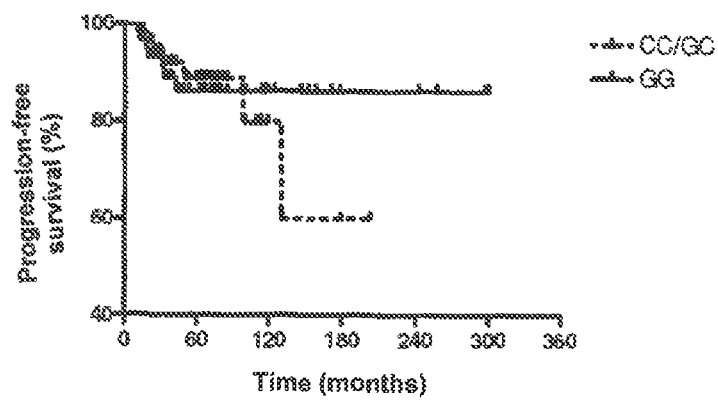

FIG. 15: Kaplan-Meier analysis regarding the survival of patients suffering from chronic lymphatic leukaemia depending on the genotype of the −7235C>G polymorphism; *: $p<0.05$.

Figure 16:
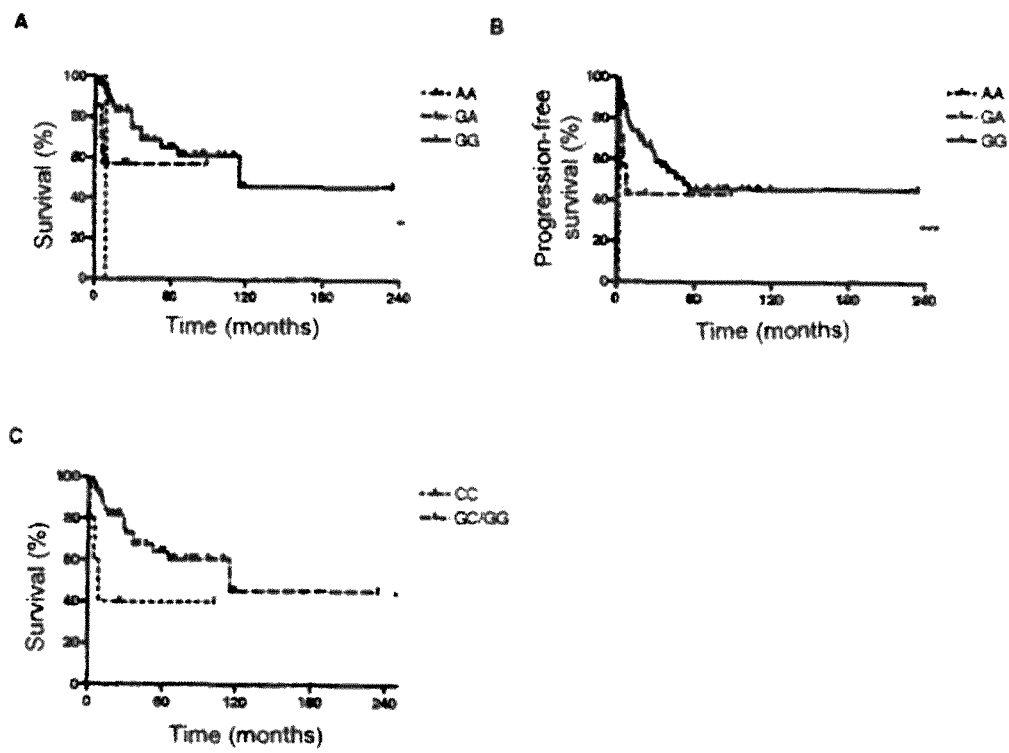

FIG. 16: Kaplan-Meier analysis regarding the survival of patients suffering from renal cell carcinoma of stages 3 and 4. A: survival depending on genotype of the −7161G>A polymorphism, B: progression-free survival depending on the genotype of the −7161G>A polymorphism, C: survival depending on the −7235C>G polymorphism; ***: $p<0.001$; *: $p<0.05$.

Figure 17:
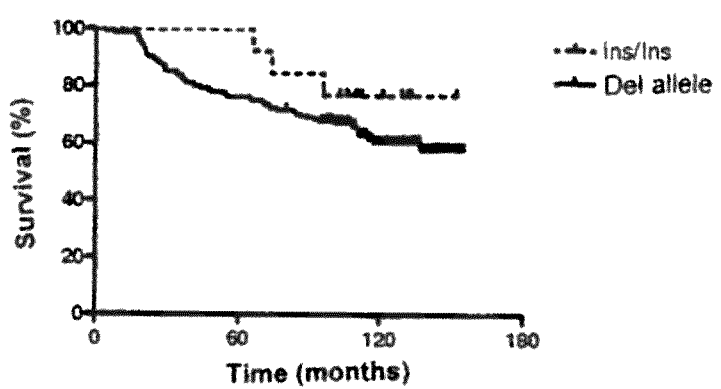

FIG. 17: Kaplan-Meier analysis regarding the survival of patients suffering from breast cancer depending on the genotype of the −10649-(−10621)del29 polymorphism.

Figure 18:
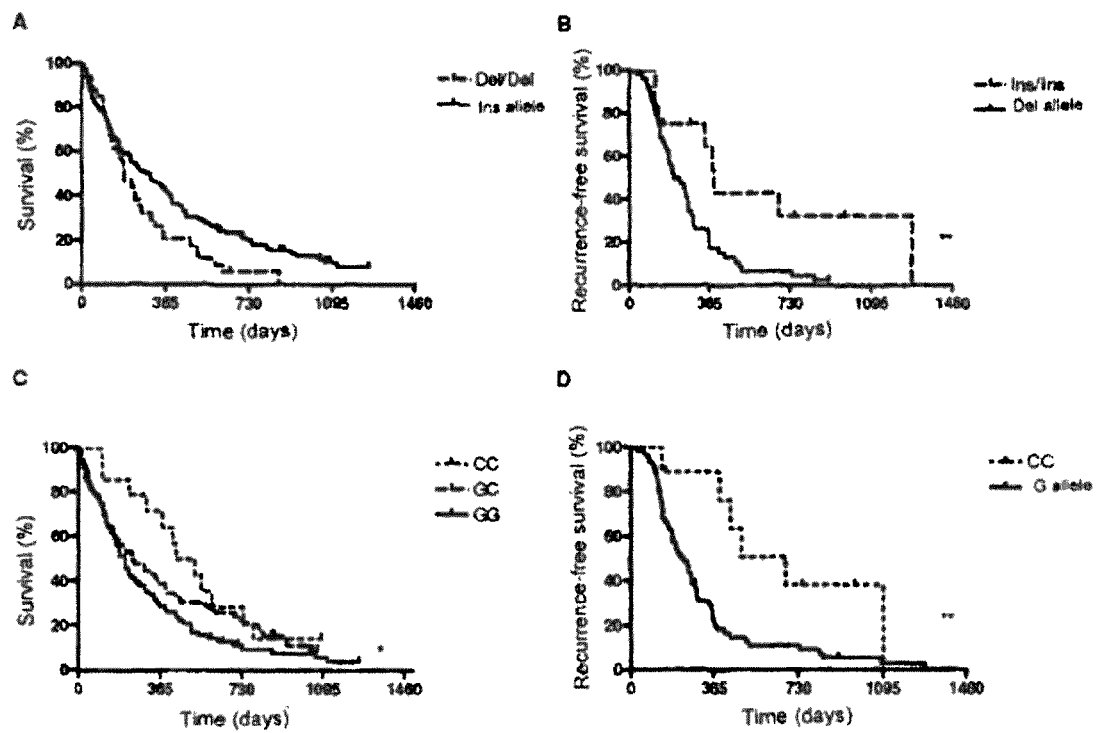

FIG. 18: Kaplan-Meier analysis regarding the survival of patients suffering from glioblastoma. A: survival, B: recurrence-free survival depending on the genotype of the −10649-(−10621)del29 polymorphism, C: survival, D: recurrence-free survival depending on −7235C>G polymorphism; **: $p<0.01$; *: $p<0.05$ FIG. 19: Kaplan-Meier analysis regarding the survival of patients suffering from prostate carcinoma depending on the genotype of −7161G>A polymorphism; **: $p<0.01$ FIG. 20: Graph illustrating the correlation between the genotypes of the −7235C>G polymorphism and the survival of patients with colorectal carcinoma.

Figure 21:
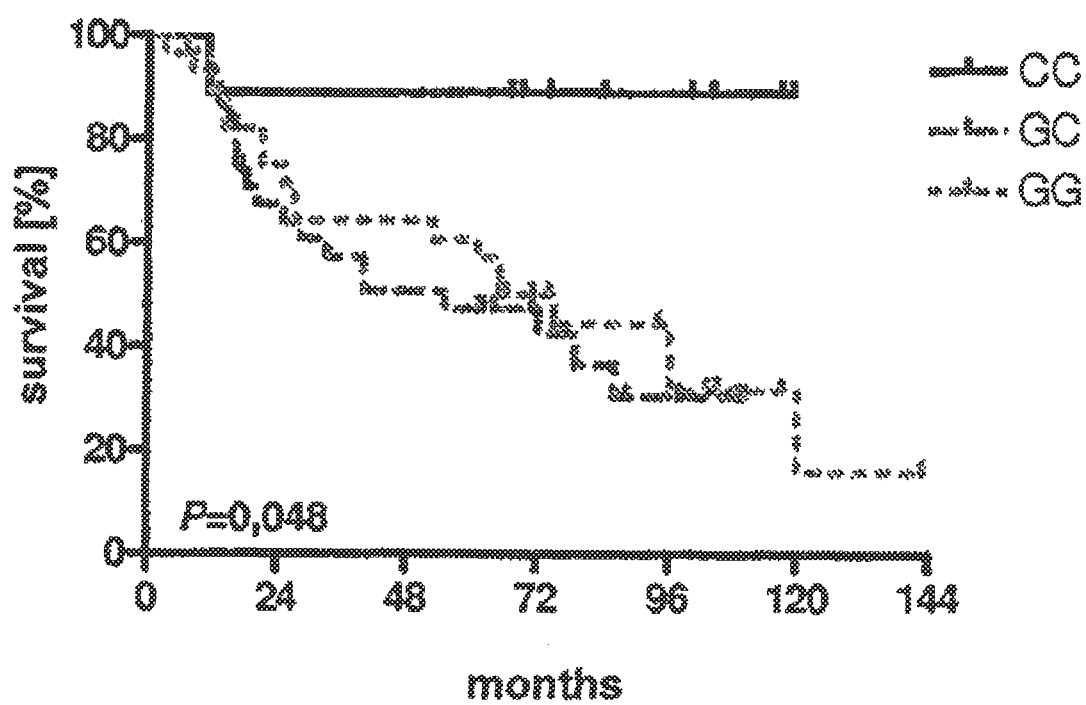

FIG. 21: Graph showing the survival curve of patients with laryngeal carcinoma who were given a combined radio-chemotherapy.

Functional Significance of the Promoter Polymorphisms in the Gene CHK2

An analysis as to which functional modifications must be attributed to the promoter polymorphisms in the gene CHK2 was carried out. A correlation with alternative splicing, tissue-specific expression or an overexpression of the CHK2 protein depending on genotypes and haplotypes of the promoter, respectively, are possible. In this context, first, an analysis was carried out using a computer program to find out whether the observed nucleotide exchanges can influence the binding of transcription factors. Transcription factors bind to specific consensus sequences and may increase or reduce promoter activity so that this results in an increased or reduced transcription of the gene and the expression of the encoding protein is increased or reduced. As shown in FIG. 7, all above-mentioned promoter SNPs are located in a consensus sequence for binding sites of different transcription factors (e.g. p53, NF-kB or Mef2) the binding of which can be impaired by polymorphisms. The occurrence of specific genotypes has the effect that these binding sites are lost or that they are newly formed due to the modification of their consensus sequences. For an experimental analysis of this effect, a so-called EMSA (electrophoretic mobility shift assay) is carried out. In this assay, short nucleic acid segments containing the relevant polymorphism are incubated with cell nuclear extracts. Then transcription factor proteins contained in these extracts bind to the nucleic acid segments with different intensity. Subsequently, the binding to the DNA is visualised using an X-ray film. Strong binding will result in an intensive band. FIG. 8 shows the result of this assay with specific constructs containing either the C or the G allele of the −7235C>G polymorphism. The presence of the C-construct band shows binding of a transcription factor to this region. The G-construct does not have this band, which shows that no transcription factor binds to this allele. The decrease in the intensity of the band by a specific oligonucleotide shows that the binding transcription factor is a specific binding. FIG. 9 shows the result of this assay with specific constructs which either contain the insertion allele or the deletion allele of the −10649-(−10621)del29 polymorphism. Both alleles result in the binding of a transcription factor with which the second allele can compete. However, the transcription factors are different in this case. FIG. 10 moreover shows that the binding of the transcription factor to the deletion allele results in increased promoter activity than in the deletion allele.

Subsequently, the expression of CHK2 at mRNA level was analysed in human tissue by means of real-time PCR. For this purpose, mRNA from human tissue obtained from breast cancer surgery as well as from blood cells from patients suffering from leukaemia was taken and transcribed by means of reverse transcriptase into cDNA. The method is known to those skilled in the art. Subsequently, the expression level was determined using real-time PCR (Taqman method) and compared to the expression level of the housekeeping gene β-actin.

Figure 11:
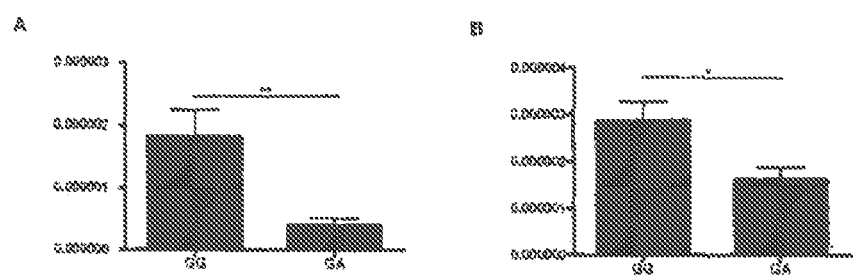
Figure 12:
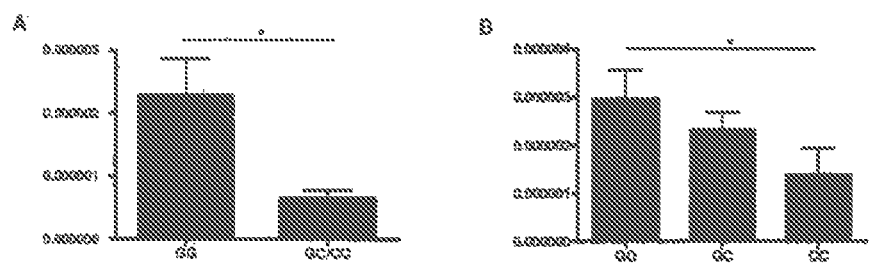
Figure 13:
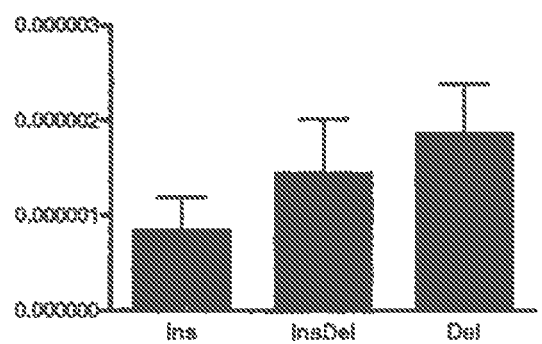

The results are shown in FIGS. 11 to 13. FIG. 11A shows that the GG genotype of the −7161G>A SNPs has significantly higher mRNA expression in breast cancers that the GA genotype. FIG. 11B also shows increased mRNA expression for the GG genotype in CLL patients. Polymorphism −7235C>G also shows an allele-dependent difference in gene expression. As illustrated in FIGS. 12A and 12B, C-allele carriers have significantly less CHK2 mRNA than carriers of the GG genotype.

This applies to patients suffering from breast cancer and to CLL patients. FIG. 13 represents increased mRNA expression for the homozygous deletion in patients suffering from breast cancer. The homozygous insertion has the lowest expression. The heterozygous genotype shows an intermediate value. In this context, a gene-dosage effect can be observed.

Thus, it was proven that there are gene modifications in the gene CHK2 which cause a change of the expression of CHK2 in carcinoma tissue. These may be the promoter polymorphisms described above or polymorphisms that show linkage disequilibrium with respect to SNPs. Thus, subject matter of the present invention also includes quantifying the expression of CHK2, associating it to known polymorphisms of CHK2 and discovering new, better suited polymorphisms and validating these.

The findings regarding genotype-dependent expression of CHK2 in human carcinoma tissue as shown herein is extremely significant, since reduced CHK2 activity can cause instability of microsatellites and chromosomal instability, which both are part of the characteristics of genomic instability and, thus, favour oncogenesis and have a negative effect on tumour progression (Ahn et al. The CHK2 protein kinase. 2004 DNA Repair 3: 1039-1047). Moreover, this genotype-dependent gene expression of CHK2 can have an effect on the response to a therapy with CHK2 inhibitors. It is to be expected that lower gene expression that is predisposed due to a specific genotype, e.g. the CC genotype of the −7235C>G polymorphism, shows a stronger response to CHK2 inhibitors than other genotypes. Thus, gene modifications in the gene CHK2 can be used to predict the response to a cancer therapy in order to discriminate for example between responder and non-responder. These gene modifications can also be used in dose finding and/or for predicting the occurrence of undesired side effects of drugs. Such cancer therapies can be drug-based in the broadest sense, i.e. by supplying substances to the body, or these means of cancer therapy can have a physical effect (such as radiation, heat, cold).

Thus, we expect an effect on the course of diseases, in particular in the case of tumour diseases, as well as a modified response to substances which influence the regulatory cascade of CHK2 or to substances which directly inhibit CHK2.

Use of Gene Modifications in CHK2 for Predicting of Disease Risks and the Course of Diseases Due to the key role of checkpoint kinase 2 in the regulation of the cell cycle, an essential subject matter of the invention is the possibility to predict in general disease risks and the course of diseases by using gene modifications in CHK2.

The multistep development of cancer reflects the accumulation of genetic modifications which lead to the transformation of normal cells into cancer cells and of normal tissue into benign and possibly malignant, invasive tumours. The accumulation of alterations in tumour suppressor genes and proto-oncogenes speeds up tumour genesis and can influence radiotherapy as well as chemotherapy. However, it becomes increasingly clear that impaired DNA repair mechanisms as well as checkpoints are the cause of increased genomic instability of tumours. Since checkpoints play a central role in the maintenance of genomic integrity, it can be expected that the course of various and very different tumour diseases is influenced by genetically determined, reduced activatability of checkpoints. This means that expression modifications of proteins that are expressed in all human body cells and protect the cell against DNA damages regulate cell functions that have a decisive influence on all physiological and pathophysiological processes or at least modulate these. Furthermore, responses to pharmaceuticals are influenced in a specific manner. This applies to desired but also to undesired drug effects.

It was repeatedly postulated in scientific literature that functional modifications of checkpoint proteins have a sustained effect on various diseases and on the course of various diseases since they are pathways that are phylogenetically maintained to a high degree. Gene modifications of this kind can be structure-modifying mutations in the checkpoint proteins which, for example, reduce the activation of the proteins by phosphorylation or reduce substrate selectivity. Furthermore, the expression level can be modified, whereby the initiation of the subsequent reaction cascades which, e.g., induce apoptosis is reduced or splicing variants with modified function can occur. All these modifications are considered to be a genetic predisposition to cancer.

From the examples mentioned, it is clear that
1. gene modifications in genes which encode ubiquitously expressed proteins, influence or cause various diseases and various risks of disease and
2. checkpoint proteins are part of the complex network for the maintenance of genomic integrity in the human body.

Diseases that involve a gene modification in the gene CHK2 and are, for example, determined by a modified expression level of the CHK2 protein are for example benign and malignant neoplasias of any parent tissue.

Consequently, an essential subject matter of the invention is the provision of diagnostically relevant gene modifications in the gene CHK2 as prognosis factor for all human cancer diseases. This will be illustrated in the following using selected examples.

Colorectal Carcinoma—

The colorectal carcinoma is the most common tumour type in the gastrointestinal tract and one of the main causes of tumour-related death worldwide (12-15% of total cancer mortality). The medium five-year survival rate after tumour resection is only 50%. The standard method for predicting the course of disease is the TNM or UICC stage system. Patients at UICC stages III or IV have in general worse prognosis than patients at UICC stages I or II. Adjuvant chemotherapy is applied in the case of metastasizing colorectal carcinomas (UICC stages III and IV) and can enhance the local effect of radiotherapy. The majority of these patients develop recurrences and metastases, which requests intensive follow-up care. Thus, it is important to identify and establish suitable markers which are capable of predicting the further course of disease. Another subject matter of the invention is to use the gene modifications in CHK2 so as to be able to predict the further history of the colorectal carcinoma.

FIG. 14 shows a difference regarding the survival depending on the −7161G>A polymorphism in patients suffering from colorectal tumours at stages UICC III and IV.

Patients with the GG genotype survive longer than patients having the heterozygous GA genotype.

Chronic Lymphatic Leukaemia—

A characteristic of chronic lymphatic leukaemia (CLL) is the high number of degenerated lymphocytes. A total of 30% of all leukemic diseases are chronic lymphatic leukaemias. The average age of onset is 65 years. CLL can be benign up to 20 years, i.e. patients do not have any symptoms apart from enlarged lymph nodes, fatigue and loss of appetite. Treatment is only started when the number of lymphocytes greatly increases, the ratio of erythrocytes and thrombocytes decreases or other complications occur. Early treatment has no effect on the course of the disease. The most important therapeutic measure is chemotherapy. The more the disease is advanced, the more important the health impairments due to modifications of the organic system. Depending on the Binet stage of the disease, the physician can establish a prognosis estimate. The stage of CLL is characterised among others by the number of lymphocytes in blood and bone marrow, by the size of spleen and liver and the presence of anaemia. CLL results in modifications in the immune system so that humans suffering from this disease have a greater risk to develop other types of cancer. However, patients show very different courses of disease at the same stage of the Binet system. The problem underlying the invention is to show that gene modifications in the gene CHK2 are suited to predict the course of the disease.

For this purpose, CLL patients were genotyped with regard to the described gene modifications in CHK2 and the gene status was correlated with the progression-free survival. FIG. 15 shows the survival depending on the −7235C>G polymorphism. Patients who are carrier of the CC/GC genotype survive for a shorter period than patients who are homozygous GG.

Renal Cell Carcinoma—

In the case of renal cell, the chance of recovery depends on tumour size and tumour proliferation. Patients without metastases have ten-year survival rate of up to 80%, however, with significant inter-individual variability. Due to the use of ultrasound technology which is common today, many tumours are detected at an early non-metastasized stage and can be treated in time. If distant metastases are present, it is possible to combine surgical removal of the kidney with subsequent immune therapy with interleukin-2 or interferon-alpha. This improves the defence against tumour cells of the body. In the case of metastasised renal cell carcinoma, the combination of interferon, interleukin-2 and 5-fluorouracil can achieve a response rate of 36% in studies. At present there are no predictive markers for the survival of patients suffering from renal cell carcinoma.

FIG. 16A show the survival depending on the −7161G>A polymorphism. Patients with the GG genotype survive for a significantly longer period than patients with the GA and AA genotypes (p<0.05). The average time period until death is 115 months for GG carriers, for patients with AA genotype however only 9 months. Similar data apply to progression-free survival in correlation with −7161G>A polymorphism (FIG. 16B). Also in this case, patients having the GG genotype show the lowest progression over the period of observation. The average progression-free survival is 52 month for GG, however only 2 months for AA (p<0.001). The −7235C>G polymorphism was also associated with survival (FIG. 16C). Carriers of the G allele showed a longer survival period than patients having the CC genotype (p<0.05).

Breast Cancer—

Breast cancer is the most common tumour of the female population in Europe and in the USA. It affects 7 to 10% of all women and accounts for 25% of the total female cancer mortality. The aetiology of breast cancer is still unknown, however, risk factors have been described, such as family disposition, radiation exposure or oestrogen influence. Most of the patients have an invasive carcinoma. With a few exceptions, any operable breast cancer is treated surgically, even if distant metastatization has been detected. The variably radical initial surgical treatment results in variations of the locoregional recurrence rate but not of the long-term chance of survival. Moreover, recurrences or distant metastases may quite often become manifest only five or even ten years later. For this reason, it is important to detect these lesions early and to closely monitor the patients in aftercare.

Follow-up examinations are performed in regular intervals, in case of interim suspicion even up to ten years after surgery. So far, there are hardly any valid markers which are predictive with respect to the further course of the disease. Thus, at the time being, the classic factors such as tumour size, metastatization, involvement of the lymph nodes, hormone receptor status etc are used for prognosis. Genetic markers for survival probability and response to therapy would substantially improve the care of patients suffering from breast cancer. The problem underlying the invention is to show that the use of gene modifications in CHK2 is suited to predict the further course of the disease.

FIG. 17 illustrates the survival of patients with breast cancer in correlation with the −10649-(−10621)del29 polymorphism. Patients with the homozygous insertion show highest survival rate when compared to patients who are carrier of at least one deletion allele.

Glioblastoma—

Gliomas mainly occur in adults. The aetiology is unknown. The histology of gliomas is characterised by malignant progression, diffuse invasion and high heterogeneity. The most common malignant glioma is the glioblastome (WHO grade IV). It often spreads via the Corpus callosum into the other hemisphere of the brain. A curative surgical therapy is only possible in case of grade I gliomas (pilocytic astrocytomas). All other gliomas recur. At present, they are incurable. The median survival time is 6 to 8 months for glioblastoma. Without post-surgical radiation, the median survival time is only 2 to 3 months. At present, there are no markers that are predictive with respect to the course of this severe disease.

Genetic markers for the prognosis of survival and responses to therapy would substantially improve the care of patients suffering from glioblastoma. The problem underlying the invention is to show that the use of gene modifications in CHK2 is suited to predict the further course of the disease.

FIGS. 18A and B show that the −10649-(−10621)del29 polymorphism has an effect on the course of disease in the case of glioblastoma.

Patients with an insertion allele show longer survival and also longer recurrence-free survival. On average, patients who are homozygous for the insertion, are free of recurrence for 390 days, however, patients with a deletion allele are free of recurrence for 206 days only. The −7235C>G polymorphism also correlates with the course of disease (FIGS. 18C and D). Patients with the CC genotype survive longer than patients with the GG genotype and heterozygous subjects have survival periods between these, which is in favour of a gene-dosage effect. The recurrence-free period of patients with the CC genotype is also longest when compared to patients who are carriers of the G allele.

Prostate Carcinoma—

The prostate carcinoma is the second most common malignoma among male patients. It accounts for 9-11% of all tumour diseases with increasing incidence. More than 50% of the cases are patients who are more than 70 years old. For early diagnosis, it is possible to measure the level of prostate-specific antigen (PSA). Early diagnosis examinations of this kind are useful for men who are more than 50 years old and have a life expectancy of more than 10 years. The significance of the PSA value is, however, disputed. The PSA has to be taken prior to the rectal examination since otherwise the PSA values are falsely high. Moreover, increased PSA values can occur with benign prostatitis. At early stages, the prostate carcinoma is mostly asymptomatic since it develops at sites remote from the urethra. For this reason, self-examination for early diagnosis is not possible. The five-year survival rate is 60% for a prostate carcinoma with Flocks stage C, however, after ten years the survival probability is only 30% and after 15 years it is only 20%. So far, there are hardly any valid markers which are predictive with respect to the further course of the disease.

Figure 19:
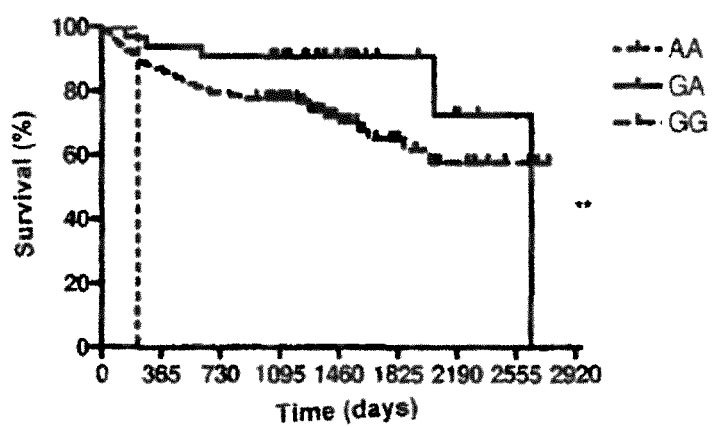

Genetic markers for survival probability and response to therapy would substantially improve the care of the patients. FIG. 19 shows the survival in correlation with the −7161G>A polymorphism. Patients with at least one G allele show better survival than patients with the AA genotype. Whereas the median survival of G-allele carriers is 2650 days, carriers of the AA genotype show a survival of only 220 days. These results show unambiguously the usability of gene modifications in the gene CHK2 for the purposes described herein. A priori, there is no connection between these diseases.

Use of Gene Modifications in the Gene CHK2 for Predicting the Course of Diseases and Responses to Therapy Pharmacogenetics within the meaning of the invention relates to the diagnosis of efficacy of pharmaceuticals, the potency and efficiency of pharmaceuticals and the occurrence of undesired effects. For the definition of the efficacy of pharmaceuticals and/or the occurrence of undesired side effects, various parameters are used in addition to the specific substance properties of the chemically defined products. Two important parameters, the achievable plasma concentration and the achievable plasma half life, determine the efficacy or inefficacy of pharmaceuticals or the occurrence of undesired effects to a large extent. The value of plasma half life is inter alia determined by means of the rate at which specific pharmaceuticals are metabolized in the liver or other body organs into effective or ineffective metabolites and at which they are eliminated from the body, wherein the elimination may take place via the kidneys, breathing air, sweat, seminal fluid, faeces or other body secretions. Moreover, in the case of oral administration, the efficacy is limited by the so-called "first-pass effect" since, after the absorption of pharmaceuticals via the intestine, a certain amount of the pharmaceutical is metabolized into ineffective metabolite in the liver.

Mutations or polymorphisms in genes of metabolizing enzymes can modify the activity of these in such a way that their amino acid composition is modified whereby affinity to the substrate to be metabolized is either increased or decreased and, thus, the metabolism may be accelerated or decelerated. In a similar way, mutations or polymorphisms in transporter proteins can modify the amino acid composition in such a way that the transport and, consequently, the elimination from the body is accelerated or decelerated.

For the selection of a substance that is optimally suited for a patient, the optimal dosage, the optimal dosage form and the avoidance of undesired side effects, part of these harmful or lethal, knowledge of genetic polymorphisms or mutations which result in modification of the gene products is of extreme importance.

The Significance of Checkpoint Kinase 2 for Chemotherapeutic Drug and Radiation Therapy Genetic instability is a characteristic of all tumours and also plays a role in the oncogenesis, progression and the development of resistance against pharmaceuticals. Most of the tumour cells have a defect G1-S checkpoint, which provides them with a survival advantage. However, this defect implies that tumour cells highly depend on the G2 checkpoint if stimuli are present which threaten genomic integrity. CHK2 is responsible for the maintenance of the G1 checkpoint if DNA damages occur. Consequently, the activation of CHK2 and, thus, the restoration of the G1 checkpoint offer the possibility to avoid therapy resistances. It was already shown that the loss of CHK2 causes resistance against radiation. This resistance might be reversed by CHK2 activators. Since CHK2 also influences the G2 checkpoint, its inhibition and, thus, the deactivation of the G2 checkpoint can provide the possibility that DNA damages and modifications caused by genotoxic substances can accumulate and that they cause the death of the tumour cell.

If gene modifications in CHK2 which influence gene expression occur, this has effects on the efficacy of these CHK2 inhibitors. It is to be expected that patients with genotype-dependent lower CHK2 expression show a better response to the inhibitors than patients with a higher CHK2 expression. Moreover, this means that it is possible to influence the combination therapy of CHK2 inhibitors using chemotherapeutic and immunotherapeutic agents and/or radiation. The same applies to CHK2 activators. It is to be expected that patients with higher genotype-dependent CHK2 expression show a better response to activators than patients with a lower CHK2 expression. This results in the possibility of an individual diagnostic of the general potential of response to these anti-cancer drugs and therapeutic measures and the possibility of an individual prediction regarding the risk of undesired effects of these therapies.

The Genotype-Dependent Diagnosis of CHK2 Expression Allows a General Diagnosis of the Efficacy of Chemotherapeutic Agents and Radiation, their Optimal Dosage and the Occurrence of Side Effects.

Chemotherapy uses substances the damaging effect of which is targeted as precisely as possible to specific cancer cells and kill these or inhibit their growth. A specific dose of a cytostatic agent can only kill a specific percentage of target cells which remains unvaried with progressing therapy. For this reason, chemotherapy must not be reduced in the course of treatment, even if the tumour is no longer detectable. It is rather to be expected that a reduced treatment will select the resistant tumour cell clones. Chemotherapy is applied in short intervals and, in almost all cases, two or more cytostatic agents are combined in order to increase efficacy. For this reason, the therapy also causes side effects which are classified according to the Common Toxicity Criteria. These criteria include: the number of leukocytes and platelets, nausea, vomiting, diarrhea and stomatitis.

Radiotherapy is the application of ionising highly energetic radiation to cure malignant tumour. Such malignant tumours are often treated with combined chemo- and radiotherapy. A multitude of tumour diseases can be cured in this way also at advanced stages. In order to limit the side effects, radiation is distributed to numerous daily single doses and administered over several weeks. Nonetheless, side effects such as reddening, nausea, diarrhea or alopecia occur depending on dosage, penetration depth and number of single doses.

The invention is based on the development of a method which is generally suited to the diagnosis of the activatability of checkpoint kinase 2 and, thus, of the G1 and G2 checkpoints. For this purpose, one or more polymorphisms in the gene CHK2 are analysed. High expression involves predictably increased activatability of the checkpoints and, thus, provides sufficient time to carry out repair mechanisms on the DNA after damage. With lower CHK2 expression, the checkpoints are less activatable and DNA damages are not at all or not sufficiently repaired. Thus, the detection of the presence of polymorphisms in CHK2 diagnosis of the efficacy and undesired effects of drugs, in particular of cytostatic drugs, and of other therapy forms which damage the genome of the tumour cells, such as radiation. Furthermore, such polymorphisms in CHK2 can be used to diagnose the effects of pharmaceuticals which are combined with a CHK2 inhibitor. In addition, the diagnosis of the allele or haplotype status in CHK2 can be used to determine the individual optimum and acceptable dose of drugs.

For the diagnosis of increased or reduced activatability of checkpoint kinase 2 and the checkpoints, in particular the detection of the CHK2 polymorphisms described herein is used, either alone or in all conceivable combinations.

Furthermore, all other gene modifications in the gene CHK2 can be used which are in linkage disequilibrium with these polymorphisms and/or additionally enhance or inhibit the alternative splicing process or expression.

The gene modifications can be detected using any methods known to the person skilled in the art, such as direct sequencing, restriction analysis, reverse hybridisation, dot blot or slot blot methods, mass spectrometry, Taqman® or LightCycler® technology, pyrosequencing etc. Moreover, these gene polymorphisms can be detected at the same time according to multiplex PCR and hybridisation to a DNA chip. For the diagnosis of increased activatability of G proteins, other methods allowing the direct detection of the expression level of CHK2 or splicing variants of CHK2 can also be used.

The method mentioned are in particular suited for diagnosing the effect of substances which damage the DNA of the tumour cells. These substances include oxaliplatin, 5-fluorouracil, folic acid, irinotecan, capecitabine and cisplatin with the list being extendable at discretion. Moreover, it is possible to predict the effects of immunotherapeutic agents (e.g. interferons or interleukins) or inhibitors of signal transduction in tumour cells.

Furthermore, it is possible to predict the effects of radiotherapeutic measures such as radiation with gamma rays, X-rays, electrons, neutrons, protons and carbon ions, with the list being extendable at discretion. In a broader sense, radiation therapy also refers to the medical use of microwaves and thermic waves, light and UV therapy as well as treatment with ultrasound radiation.

The following Examples are to further illustrate the use of gene modifications in CHK2 for the prediction of risks of disease and courses of diseases.

EXAMPLES

Different tumour collectives and healthy controls for the CHK2 polymorphisms were genotyped and the genotype and/or allele distributions were compared. In this context, significant differences in the distribution of genotypes and alleles were observed. It is not possible to predict in general whether an increased expression of CHK2 is favourable or unfavourable. Thus, the polymorphisms in CHK2 are suited to predict a risk of disease. The risk of disease for the risk allele or for risk genotypes (alone or in combination) is indicated as "odds ratio" (OR) together with the 95% confidence interval (95% CI) and the p value.

Example 1

Patients with Colorectal Carcinoma (n=143) Vs. Controls (n=235)

| | −7161G > A | | | −7235C > G | |
|---|---|---|---|---|---|
| allele | colon carcinoma | controls | genotype | colon carcinoma | controls |
| G | 241 (84.3%) | 419 (89.2%) | CC | 8 (5.6%) | 25 (10.7%) |
| A | 45 (15.7%) | 51 (10.8%) | CG | 70 (49.0%) | 88 (37.6%) |
| | | | GG | 65 (45.5%) | 121 (51.7%) |

P = 0.050
P = 0.048

The allele or genotype distributions differ significantly (p=0.05 and 0.048, respectively);
OR A versus G=1.534 (95% CI=0.997-2.361) p=0.05;
OR CG versus CC=2.486 (95% CI=1.056-5.851) p=0.034;

Thus, an increased risk to develop a colon carcinoma can be attributed to −7161A allele carriers. Consequently, a reduced expression of CHK2 mRNA is associated with an increased risk of developing the disease.

Example 2

Figure 20:
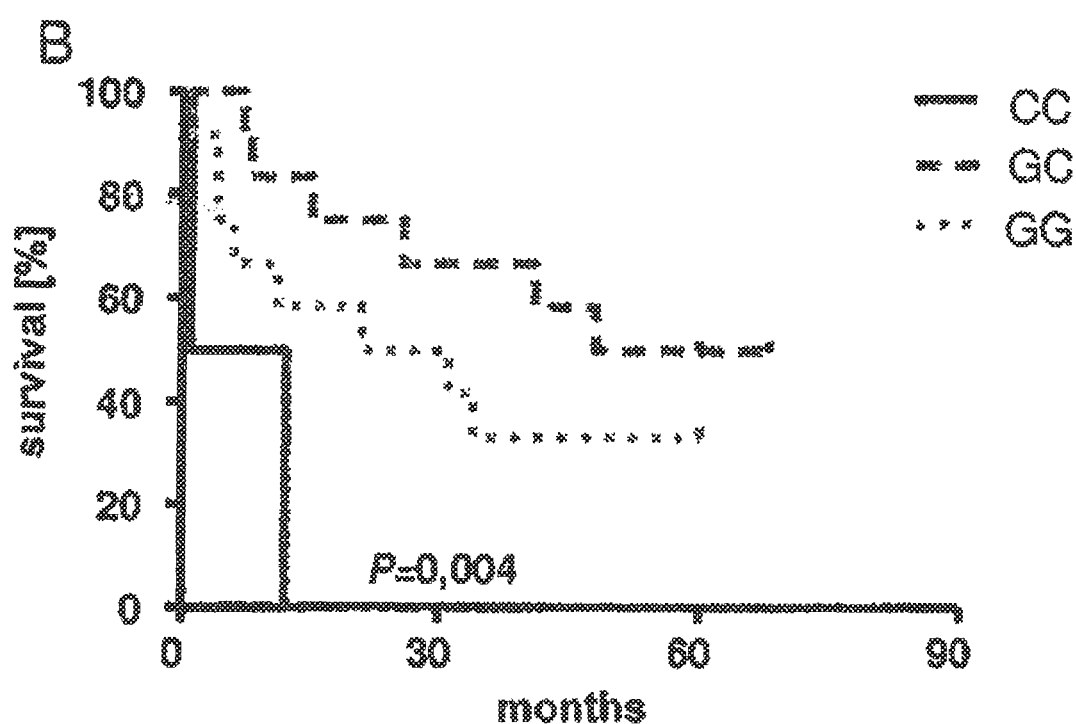

Correlation Between the −7235C>G Polymorphism and Survival in the Case of Colorectal Carcinoma It was further examined whether there is a correlation between the genotypes of the −7235C>G polymorphism and the survival of patients with colorectal carcinoma. This is illustrated in FIG. 20.

From that Figure, it can be taken that the survival rate of patients with the −7235CC genotype is clearly lower.

Thus, an increased risk to develop a colon carcinoma can be attributed to carriers of the −7161A allele and of the 72-7235CG genotype, respectively. Thus, reduced expression of CHK2 mRNA is associated with an increased risk of disease.

Example 3

Patients with Chronic Lymphatic Leukemia (CLL, n=166) Vs. Controls (n=234)

| | −7235C > G | |
|---|---|---|
| genotype | CLL | controls |
| CC | 7 (4.2%) | 25 (10.7%) |
| CG | 75 (54.2%) | 88 (37.6%) |
| GG | 84 (50.6%) | 121 (51.7%) |

Genotype distributions differ significantly (p=0.039). The following risks (OR) can be calculated for CLL:
OR CG versus CC=3.044 (95% CI=1.246-7.435), P=0.012;
OR GG plus CG versus CC=2.7 (95% CI=1.2-6.4), P=0.024;

Example 4

Patients with Glioblastoma (n=198) Vs. Controls (n=235)

| | −7161G > A | | | | |
|---|---|---|---|---|---|
| allele | glioblastoma | controls | genotype | glioblastoma | controls |
| G | 331 (83.6%) | 419 (89.2%) | GG | 145 (73.2%) | 188 (80.0%) |
| A | 65 (16.4%) | 51 (10.8%) | GA | 41 (27%) | 43 (18.3%) |
| | | | AA | 12 (8.1%) | 4 (1.7%) |

Allele and genotype distributions differ significantly (P=0.017 and P=0.039, respectively).
The following risks can be calculated:
OR A versus G: 1.613 (95% CI=1.088-2.393); P=0.021;
OR AA versus GG: 3.890 (95% CI=1.229-12.31); P=0.019;
OR AA plus AG versus GG: 3.73 (95% CI=1.2-11.8); P=0.021;

Thus, an increased risk to develop a glioblastoma can be attributed to carriers of the −7161A allele and of the −7161AA/AG genotype, respectively. Consequently, reduced expression of CHK2 mRNA is associated with an increased risk to develop the disease.

Example 5

Cox Regression for the Survival of Patients with Glioblastoma Depending on −7235C>G Polymorphism The following Table shows the results of a multivariate COX regression model for tumour-caused death of patients with gliablastoma after total resection (HR=hazard ratio, *=reference, CI=confidence interval, ED=primary diagnosis [German: Erstdiagnose], m=male, w=female [German: weiblich]

| Variables | HR (95% CI) | P value |
|---|---|---|
| -7236C > G | | |
| CC | 1* | |
| GC | 1.918 (0.73-5.02) | 0.185 |
| GG | 2.711 (1.05-7.03) | 0.040 |
| KPI | 0.600 (0.11-3.29) | 0.557 |
| Therapy | | |
| -no | 1* | |
| -radiotherapy | 0.090 (0.03-0.28) | <0.001 |
| -radio-1chemotherapy | 0.091 (0.03-0.31) | <0.001 |
| Age at the time of priman, diagnosis | 1.030 (1.01-1,05) | 0.008 |

Age at the time of oilman/ diagnosis: 58.84 ± 13.38
Gender distribution: M:65.4%; W:34.6%

In order to confirm that the analysed −7235C>G polymorphism is an independent prognostic factor for the survival of patients with glioblastoma, a multivariate COX regression was carried out which included all potential risk factors for the survival of the patients. The risk of tumour-caused death was 2.7 times higher for homozygous GG carriers than for C allele carriers (CI: 1.05-7.03; P=0.040).

As expected, the type of therapy (radiotherapy; radio-/chemotherapy) proved to be the best prognostic factor (P=<0.001), followed by the age at the time of primary diagnosis (P=0.008) and the −7235C>G polymorphism, i.e. a therapy reduces the death risk.

Example 6

Regarding the −10621del29 Polymorphism and the Survival in the Case of Glioblastoma The following Table shows the results of a multivariate COX regression model for tumour-caused death of patients with glioblastoma after total resection (HR=hazard ratio, *=reference, CI=confidence interval, ED=primary diagnosis [German: Erstdiagnose], m=male, w=female [German: weiblich]

| Variables | HR (95% CI) | P value |
|---|---|---|
| -10621del29 | | |
| Ins/Ins | 1* | |
| Ins/Del | 1.579 (0.84-2.98) | 0.158 |
| Del/Del | 2.837 (1.31-6.12) | 0.008 |
| KPI | 0.662 (0.12-3.60) | 0.883 |
| Therapy | | |
| no | 1* | |
| radiotherapy | 0.103 (0.03-0.32) | <0.001 |
| radio-/chemotherapy | 0.109 (0.03-0.37) | <0.001 |
| Age at the time of primary diagnosis | 1.033 (1.01-1.06) | 0.005 |

Age at the time of primary diagnosis: 58.84 ± 13.38
Gender distribution: M: 65.4%; W: 34.6%

In comparison to carriers of the insertion allele, patients who are carrier of homozygous deletion have a nearly 3 times higher risk to die earlier of this disease (P=0.008). As was to be expected, the type of therapy is the best prognostic factor for the survival of the patients (P=<0.001), followed by the age at the time of primary diagnose (P=0.005) and the polymorphism analysed.

Example 7

Female Patients with Breast Cancer (n=240) Vs. Female Controls (n=78)

| genotype | breast cancer | controls |
|---|---|---|
| II | 29 (12.1%) | 21 (26.9%) |
| ID | 162 (67.5%) | 38 (48.7%) |
| DD | 49 (20.4%) | 19 (24.4%) |

Genotype distribution differs significantly (p = 0.003). The following risks can be calculated: OR ID versus II: 3.087 (95% CI = 1.590-5.995), p = 0.001

Example 8

Survival of Patients with Laryngeal Carcinoma Depending on Genotypes of the −7235C>G Polymorphism FIG. 21 shows the survival curve of patients with laryngeal carcinoma who were given a combined radiochemotherapy.

Also in this case, the Kaplan-Meier curves differed significantly (p=0.048). After the application of radiochemotherapy, patients with the CC genotype showed significantly better survival than patients who carried a G allele (P=0.048). Five years later, approximately 90% of the CC carrier survived, whereas almost 70% of the G-allele carriers were dead at that point in time. This was confirmed by the COX regression.

In order to confirm that the analysed polymorphism is an independent prognostic factor for the survival of patients with laryngeal carcinoma, a multivariate COX regression was carried out. The results obtained are shown in the following Table.

| Variables | Survival HR (95% Cl) | P value |
|---|---|---|
| -7235C > G | | |
| CC | 1* | |
| GC | 9.142 (1.17-71,34) | 0.035 |

| Variables | Survival HR (95% CI) | P value |
|---|---|---|
| GG | 7.834 (1.01-60.70) | 0.049 |
| Age at the time of primary diagnosis | 1.059 (1.01-1.11) | 0.013 |
| Gender | | |
| -male | 1* | |
| -female | <0.001 (<0.001-<0.001) | 0.975 |
| AJCC | | |
| -1 | 1* | |
| -2 | 2.126 (0.49-9.28) | 0.316 |
| -3 | 3.376 (0.97-11.72) | 0.550 |
| -4 | 2.864 (0.89-9.19) | 0.077 |
| Grade | | |
| -1 | 1* | |
| -2 | 0.422 (0.05-3.56) | 0.428 |
| -3 | 0.695 (.0.07-6.56) | 0.751 |

In comparison with the homozygous CC carriers, the heterozygous GC carriers had a risk of tumour-caused death that was more than 9 times higher (CI: 1.17-71.34; P=0.035) and the homozygous GG genotypes had a 7.8 times higher risk (CI: 1.01-60.70; P=0.049). The relevant polymorphism proves to be the only independent prognostic factor. The change in risk due to the patient's age is minor. Thus, the patient's age is not relevant as prognostic factor in this case.

For patients who were given radiochemotherapy, the age at the time of primary diagnosis proved to be the best prognostic factor (P=0.013), followed by the −7235C>G polymorphism.

The field AJCC lists the tumour stages, wherein 1 indicates the most favourable stage and 4 indicates the most unfavourable stage with respect to successful treatment. Grade 1 refers to well differentiated malignant tissue ("low-grade") with high similarity to the parent tissue. Grade 3 refers to low differentiated malignant tissue.

The invention claimed is:

1. A method of treating a colorectal carcinoma of a patient, comprising:
   i) obtaining a DNA sample of the patient;
   ii) detecting a GG or GA genotype at polymorphism −7161G>A of the checkpoint kinase 2 promoter;
   iii) predicting survival of the patient, wherein the presence of a GG genotype at polymorphism −7161G>A predicts increased survival and the presence of a GA genotype predicts decreased survival; and
   iv) treating the patient with chemotherapy, radiotherapy, or a combination of both.

2. A method of treating a renal cell carcinoma of a patient, comprising:
   i) obtaining a DNA sample of the patient;
   ii) detecting the patient's genotype at polymorphism −7161G>A of the checkpoint kinase 2 promoter;
   iii) predicting survival of the patient, wherein the presence of a GG genotype at the polymorphism −7161G>A predicts increased survival and the presence of a GA genotype or an AA genotype predicts decreased survival; and
   iv) treating the patient with chemotherapy, radiotherapy, or a combination of both.

3. A method of treating a glioblastoma of a patient, comprising:
   i) obtaining a DNA sample of the patient;
   ii) detecting the patient's genotype at polymorphism −7235C>G of the checkpoint kinase 2 promoter;
   iii) predicting survival of the patient, wherein the presence of a CC genotype at polymorphism −7235C>G predicts increased survival and the presence of a G allele predicts decreased survival; and
   iv) treating the patient with chemotherapy, radiotherapy, or a combination of both.

4. A method of treating a chronic lymphatic leukemia of a patient, comprising:
   i) obtaining a DNA sample of the patient;

ii) detecting the patient's genotype at polymorphism −7235C>G of the checkpoint kinase 2 promoter;
iii) predicting survival of the patient, wherein the presence of a GG genotype at polymorphism −7235C>G predicts increased survival and the presence of a C allele predicts decreased survival; and
iv) treating the patient with chemotherapy, radiotherapy, or a combination of both.

5. A method of treating a prostate carcinoma of a patient, comprising:
i) obtaining a DNA sample of the patient;
ii) detecting the patient's genotype at polymorphism −7161G>A of the checkpoint kinase 2 promoter;
iii) predicting survival of the patient, wherein the presence of a GG or GA genotype at polymorphism −7161G>A predicts increased survival and the presence of an AA genotype predicts decreased survival; and
iv) treating the patient with chemotherapy, radiotherapy, or a combination of both.

* * * * *